United States Patent [19]
Dreher et al.

[11] Patent Number: 5,824,018
[45] Date of Patent: Oct. 20, 1998

[54] FIBRILLATION INDUCTION METHOD AND SYSTEM FOR IMPLANTABLE DEVICES

[75] Inventors: Robert Dreher, Roseville; Brian Kuhnley, Maple Grove; Conrad L. Sowder, Minneapolis, all of Minn.

[73] Assignee: Cardiac Pacemakers, Inc., St. Paul, Minn.

[21] Appl. No.: 642,806

[22] Filed: May 3, 1996

Related U.S. Application Data

[63] Continuation of Ser. No. 224,113, Apr. 6, 1994, abandoned, which is a continuation of Ser. No. 951,254, Sep. 25, 1992, abandoned.

[51] Int. Cl.$^6$ .................................................. A61N 1/36
[52] U.S. Cl. .................................................. 607/6
[58] Field of Search .......................... 605/5, 7, 8

[56] References Cited

U.S. PATENT DOCUMENTS

| | | |
|---|---|---|
| 4,800,883 | 1/1989 | Winstrom . |
| 4,850,357 | 7/1989 | Bach, Jr. ............................. 128/419 D |
| 4,998,531 | 3/1991 | Bocchi et al. . |
| 5,111,816 | 5/1992 | Pless et al. ........................... 128/419 D |
| 5,129,392 | 7/1992 | Bardy et al. ........................ 128/419 D |
| 5,215,083 | 6/1993 | Drane et al. . |
| 5,279,293 | 1/1994 | Andersen et al. ........................... 607/5 |

FOREIGN PATENT DOCUMENTS

| | | | |
|---|---|---|---|
| 0 491 649 A2 | 6/1992 | European Pat. Off. ......... A61N 1/39 |
| 0 558 353 | 9/1993 | European Pat. Off. . |

OTHER PUBLICATIONS

Bourland et al., "Sequential Pulse Defibrillation for Implantable Defibrillators," Medical Instrumentation, vol. 20, no. 3, May.–Jun. 1988, pp. 138–142.

*Primary Examiner*—Scott M. Getson
*Attorney, Agent, or Firm*—Schwegman, Lundberg, Woessner & Kluth, P.A.

[57] ABSTRACT

A method and apparatus for generating a multiphasic defibrillation/cardioversion waveform as well as a multiphasic fibrillation inducing pulse train. The multiphasic fibrillation inducing waveform being applied to the same electrodes as the defibrillation/cardioversion waveform.

14 Claims, 5 Drawing Sheets

FIBRILLATION INDUCTION METHOD AND SYSTEM FOR IMPLANTABLE DEVICES

This is a continuation of prior application Ser. No. 08/224,113, filed Apr. 6, 1994, which is a continuation of application Ser. No. 07/951,254, filed on Sep. 25, 1992, now abandoned, entitled FIBRILLATION INDUCTION METHOD FOR IMPLANTABLE DEVICES.

BACKGROUND OF THE INVENTION

The present invention relates to implanted arrhythmia control devices, and more particularly to a non-invasive method and apparatus for inducing arrhythmias after the device is implanted. More specifically, it relates to a non-invasive method and apparatus for generating fibrillation inducing pulse trains for the purpose of testing an implanted cardiovesion/defibrillator.

Ventricular fibrillation typically must be induced when an automatic implantable cardioverter defibrillator is implanted and for follow-up studies to test the effectiveness of the automatic implantable cardioverter defibrillator in defibrillating.

When implantable arrhythmia control devices are used, it is desirable to allow stimulation of the heart to induce arrhythmias after the device is implanted, without the need to introduce a separate stimulating lead/wire. That is, a non-invasive method of inducing arrhythmias is desirable.

In order to induce fibrillation for the purpose of testing an implanted arrhythmia control device, burst or ramped burst pacing at very fast stimulation rates has been used to induce ventricular fibrillation in some patients. However, due to the small energy levels involved and the relatively small size and placement of the pacing electrode system, this method does not successfully induce ventricular fibrillation. Programmed electrical stimulation or non-invasive premature stimulation has also been used to induce ventricular tachycardia, but does not always reliably induce ventricular fibrillation. Programmed electrical stimulation or non-invasive premature stimulation commonly consist of delivering a series of fixed rate pace pulses, followed by 1 to 5 pacing "extra-stimuli" at various shorter intervals coupled to the last fixed rate pulse. Both programmed electrical stimulation/non-invasive premature stimulation and burst pacing use the much smaller pacing electrodes which tend to localize the stimulation. Fibrillation is more easily induced when large portions of the heart are stimulated simultaneously.

While these prior systems generally are effective, there is room for improvement.

SUMMARY OF THE INVENTION

Accordingly, it is an object of the present invention to provide a method and apparatus for generating a multiphasic fibrillation inducing pulse train via the defibrillation/cardioversion leads and electrodes of an already implanted defibrillator to thereby test the implanted defibrillator non invasively.

Briefly, the present invention is directed to a method and apparatus for use with an implanted defibrillator, having an external programmer including telemetry means. The telemetry means is used to communicate with an implantable device incorporating a multiphasic circuitry for non-invasively delivering a fibrillation inducing pulse train via the defibrillation/cardioversion leads and electrodes of the already implanted defibrillator. In this manner, the present invention facilitates testing of an already implanted defibrillator without the need to induce fibrillation by invasive techniques.

The above and other objects and advantages will become more readily apparent when reference is made to the following description taken in conjunction with the accompanying drawings.

DETAILED DESCRIPTION OF THE DRAWINGS

Figure 1:
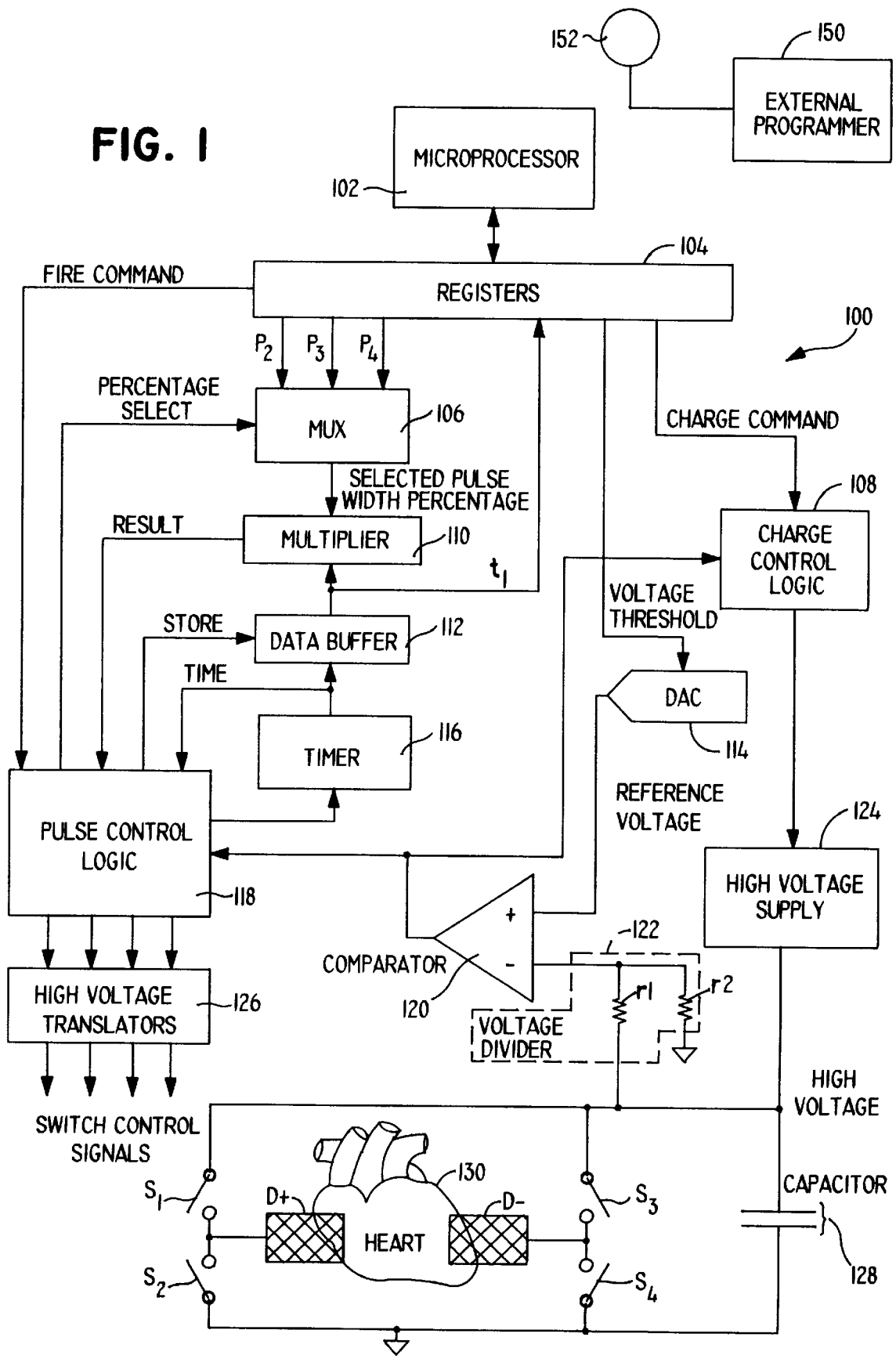
FIG. 1 is a schematic diagram of the circuitry of an implanted defibrillator, capable of generating a multiphasic defibrillation waveform, and adapted to be used with an external programmer, including telemetry means, in accordance with the present invention to deliver a fibrillation inducing pulse train via the defibrillation/cardioversion leads and electrodes of the implanted defibrillator.

FIG. 1 illustrates an implantable electrical circuitry for generating a multiphasic defibrillation waveform. An external programmer, including telemetry means, is used to communicate with the implanted circuitry to deliver fibrillation inducing pulse trains via the defibrillation/cardioversion leads and electrodes of the already implanted defibrillator in accordance with the present invention.

Figure 2A:
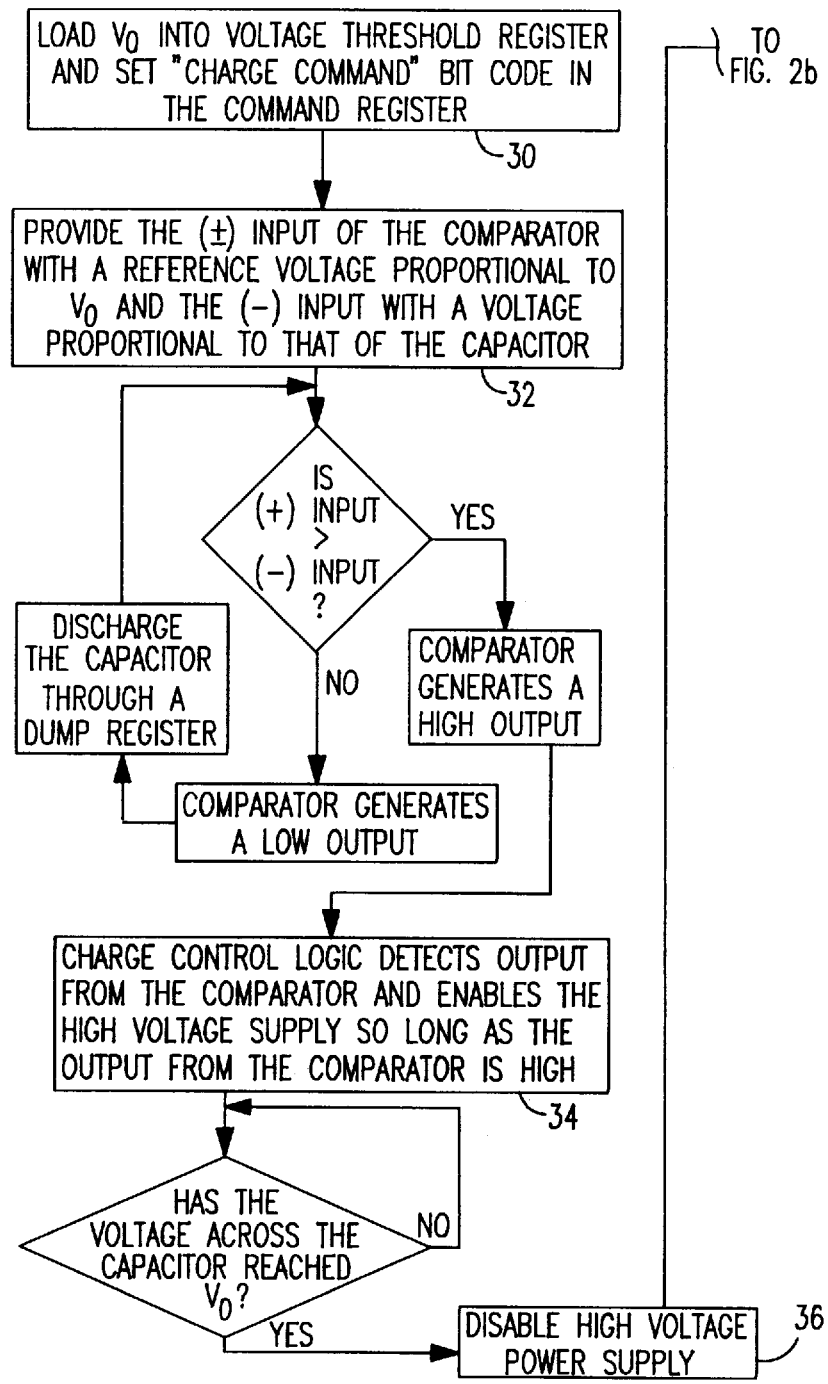
FIG. 2 is a flow chart illustrating the defibrillation operation of the circuitry shown in FIG. 1.
Figure 2B:
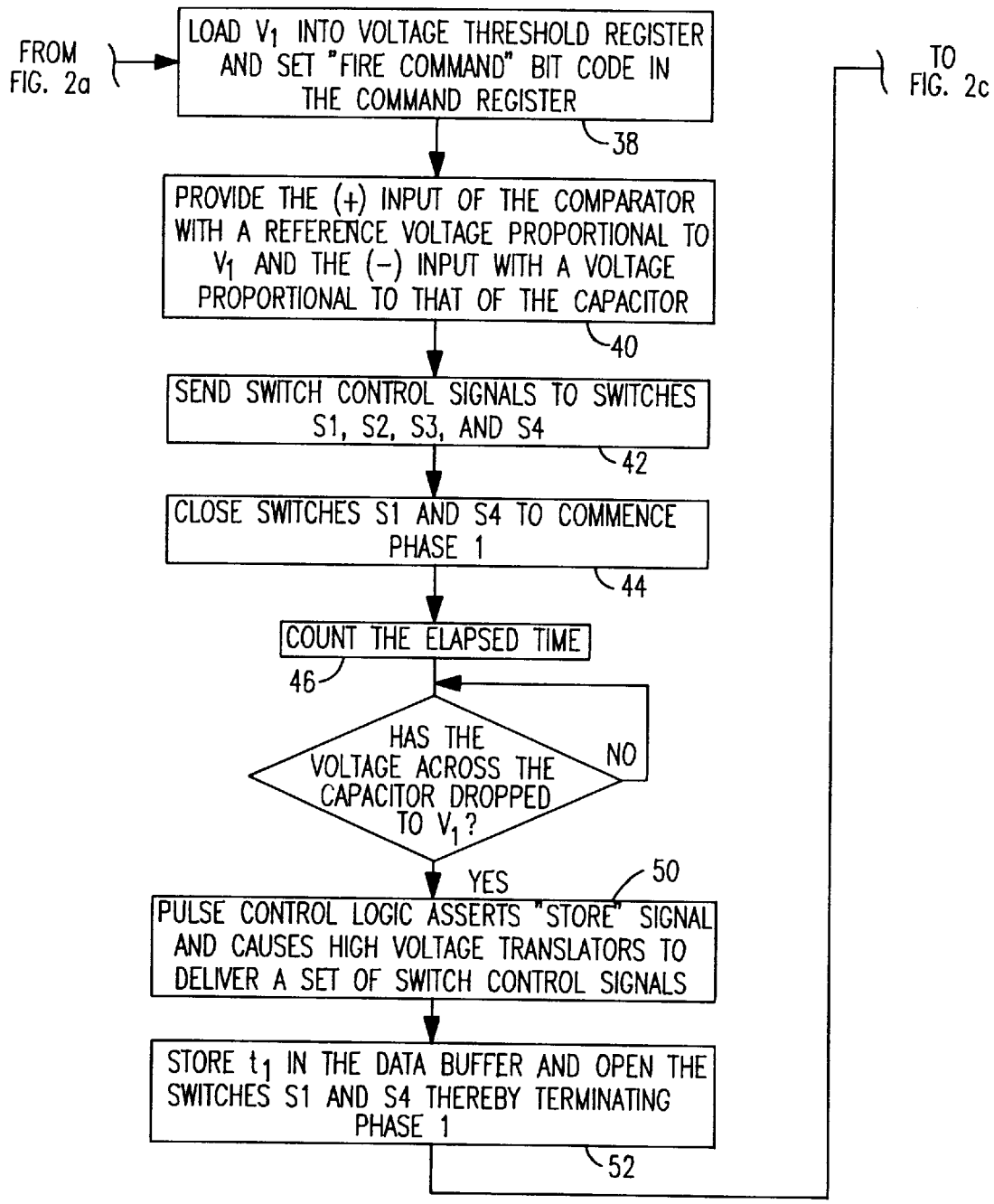
Figure 2C:
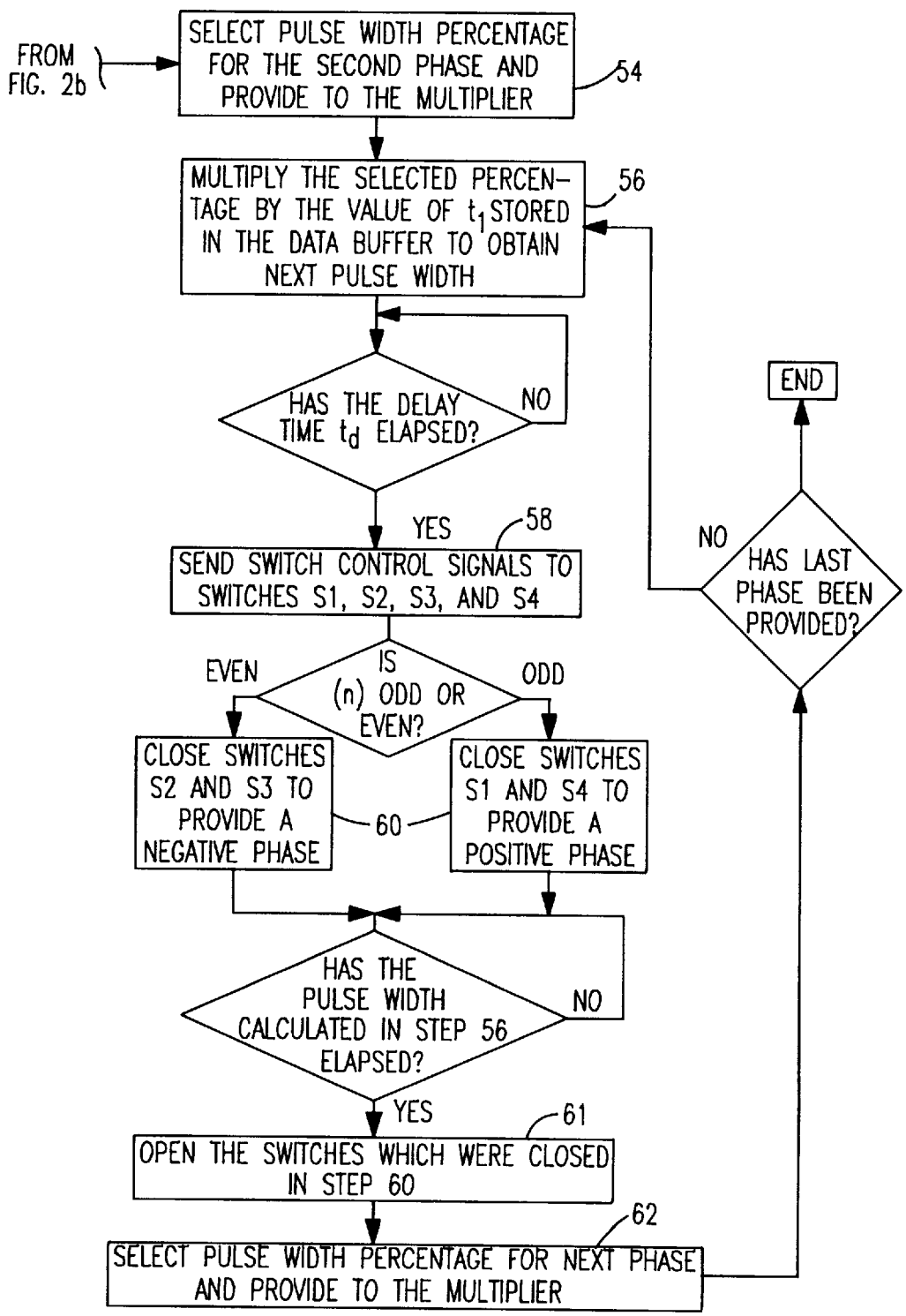

Techniques for defibrillation/cardioversion have evolved over the years from a truncated exponentially decaying waveform of a capacitor to more sophisticated waveforms, such as multiphasic waveforms. In this regard, it has been found that multiphasic waveforms often are more effective in defibrillating the heart. The circuit for generating multiphasic defibrillation waveforms shown in FIG. 1, and the operation of which is illustrated by the flow chart in FIG. 2 is more fully disclosed in U.S. patent application Ser. No. 07/951,252, entitled: Method and Apparatus for Generating Multiphasic Defibrillation Waveforms Based on Pulse Width Ratios, which was filed on the same date as this application. The disclosure of which application is hereby incorporated by reference.

In accordance with the present invention, the circuit shown in FIG. 1 for example, can be used to remotely induce fibrillation for the purpose of testing the effectiveness of the implanted defibrillator prior to discharging the patient from the hospital.

Traditionally, testing of an implanted defibrillator has been accomplished by passing a catheter into the patient and inducing fibrillation via the catheter. Recently, however, remote control of an already implanted defibrillator has been accomplished by using an external programmer device or other similar device. An external programmer includes telemetry means that provides non-invasive control and interrogation of an implanted defibrillator. The external programmer may include a telemetry wand to communicate with the implanted device via RF signals.

According to the present invention, by using an external programmer or other similar device, fibrillation can be induced via the leads and electrodes of the already implanted defibrillator.

Figure 3:
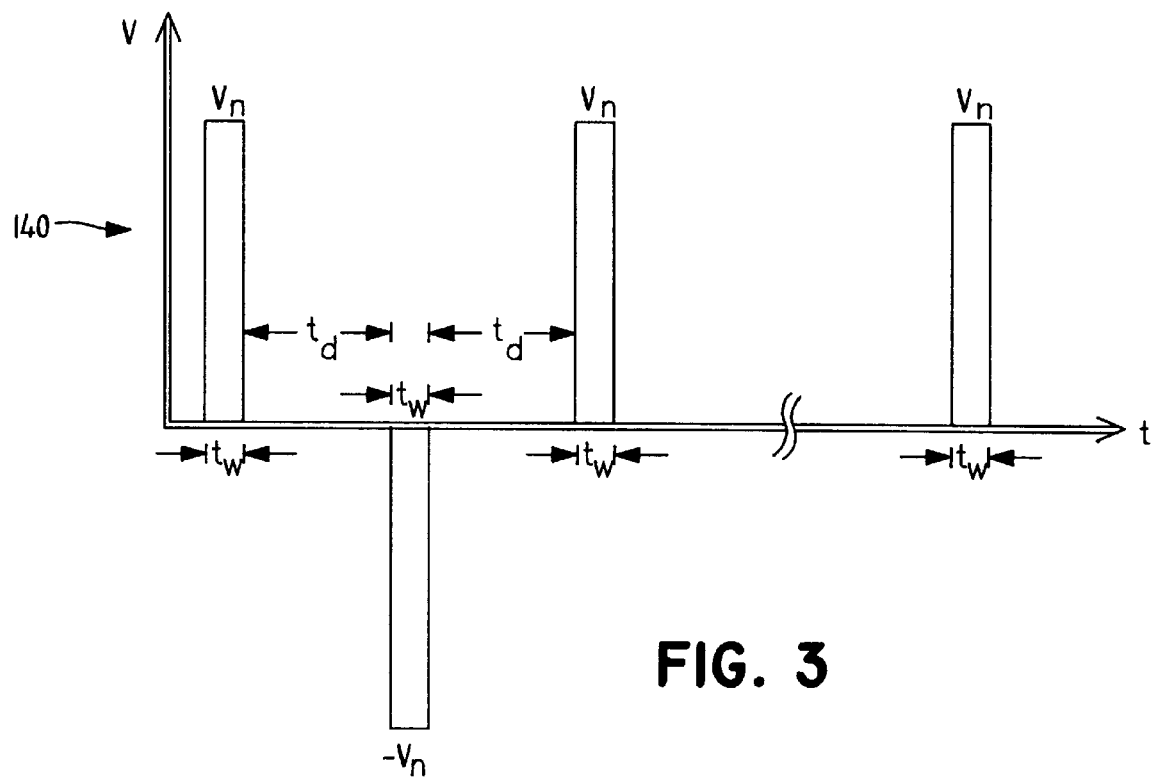
FIG. 3 is a graphical representation of a multiphasic fibrillation inducing pulse train generated by firmware in the circuitry of FIG. 1, which is used to induce fibrillation in a heart for the purpose of testing an implanted cardiac defibrillator.

With reference to FIG. 1, an external programmer 150 (or other similar device) having a telemetry wand 152 is used to non-invasively cause the circuitry 100 of the present invention to deliver a multiphasic fibrillation inducing pulse train, rather than a multiphasic defibrillation waveform. An ideally effective fibrillation inducing pulse train 140 is illustrated in FIG. 3. All of the pulses constituting the pulse train 140 have the same nominal voltage $V_n$ which is typically on the order of 15 volts on 9 volts, with successive pulses alternating in polarity between negative and positive polarity. The pulse width $t_w$ for each pulse is typically 1.1 milliseconds, while the delay time $t_d$ between successive pulses typically range from 30 to 50 milliseconds. A delay time of 30 milliseconds provides a high rate of pulses, while a 50 millisecond delay time provides a slower rate of pulses. The pulse widths are shorter than those which are used for defibrillation purposes. All pulses subsequent to the first have the same pulse widths $t_2, t_3, \ldots, t_n$ as the first pulse.

The circuitry 100 is provided with logic which, upon detecting via the external programmer 150 or other similar device the command to induce fibrillation, directly causes a pulse train to be emitted with a predetermined pulse width equal to $t_w$, a nominal voltage equal to $V_n$, and delay time equal to $t_d$. The logic can accomplish this by causing the charge control logic 108 to charge the capacitor 128 to a predetermined voltage equal to or slightly higher than $V_n$. Next, the logic operates the circuitry 100 of FIG. 1 causing switches s1 and s4 to close for tw milliseconds, then causing the switches to open for the delay time td and thereafter closing switches s2 and s3 for tw milliseconds, this process being repeated by the logic until a predetermined period of time equal to the desired duration of the pulse train (preferably 2–5 seconds) has elapsed. In this manner, the pulse train is provided without having to detect any voltages other than the starting voltage of the capacitor.

Figure 4:
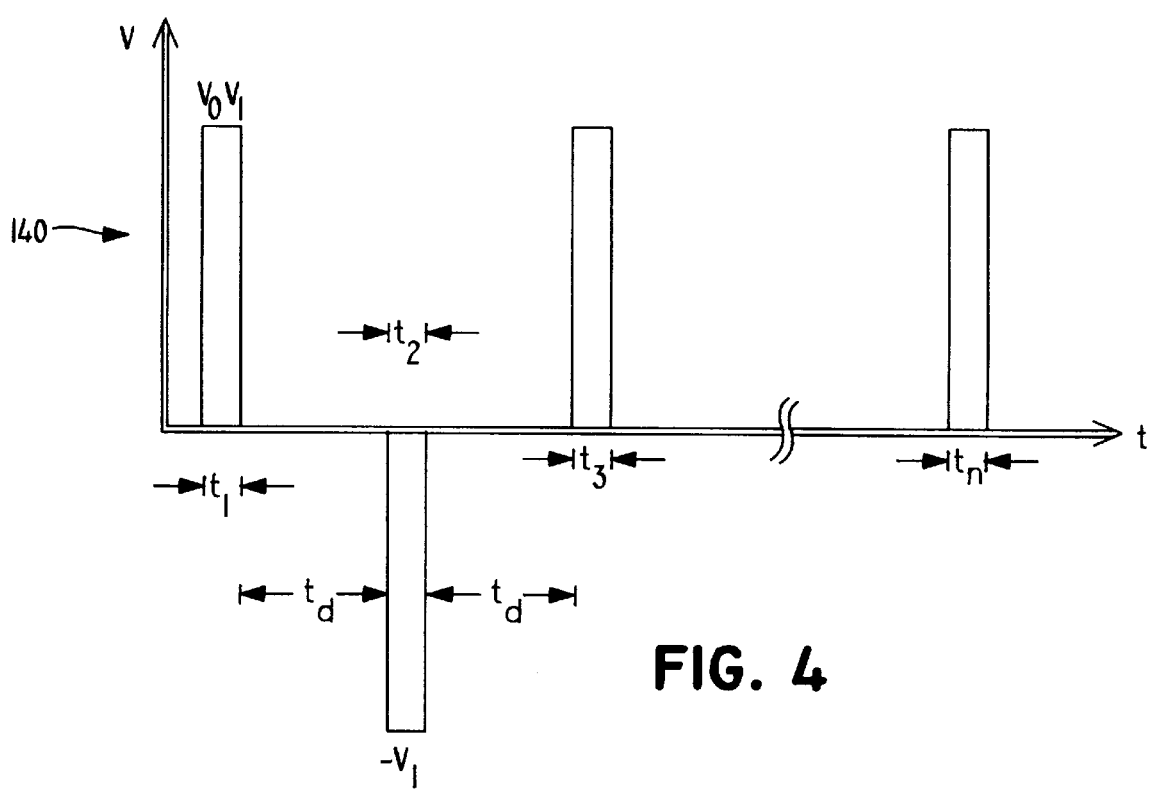
FIG. 4 is a graphical representation of an approximation of the fibrillation inducing pulse train shown in FIG. 3, which can be generated by utilizing the ratiometric capabilities of the circuitry of FIG. 1.

Alternatively, FIG. 4 illustrates a close approximation 140' of the pulse train 140 of FIG. 3, which can be generated by by using ratiometric capabilities of the circuitry 100. This approximation 140' is primarily achieved by choosing values of $V_0$ and $V_1$ which, in addition to being slightly greater than $V_n$, are very close to one another such that a shorter pulse width $t_1$ (comparable to $t_w$, and shorter than that which is used for defibrillation purposes) is achieved for the first pulse. Likewise, the pulse width percentages $P_2, P_3, \ldots, P_n$ are all programmed to equal 100 percent such that all pulses subsequent to the first have the same pulse widths $t_2, t_3, \ldots, t_n$ as the first pulse.

The approximated fibrillation inducing pulse train 140' can also be generated without the need for programming the pulse width percentages. Instead, the circuitry 100 can be provided with logic which upon sensing via the external programmer 150 or other similar device the need to induce fibrillation, causes the contents of the data buffer 112 to be provided to the pulse control logic 118 in place of the result from the multiplier 110. Consequently, rather than providing the result from the multiplier 110 to the pulse control logic 118, the actual value of $t_1$ from the data buffer 118 is provided. Hence, all subsequent pulses are automatically delivered with the same pulse width as $t_1$.

Furthermore, modifications may be made to the circuitry 100 shown in FIG. 3, for the purpose of delivering fibrillation inducing pulse trains, without departing from the scope and spirit of the present invention. For instance, the pulses or "mini-shocks" can be delivered in alternating polarity as set forth above, or all in the same polarity. Each pulse is delivered as a monophasic fixed pulse width shock, with short charge cycles between pulses. The shocks are delivered to the defibrillation electrodes by the four switch $S_1, S_2, S_3. S_4$ switch bridge network. Such use of the same output circuit for the fibrillation inducing pulses as the normal defibrillation pulse delivery has not previously been provided. The very high rate delivery through the larger shocking electrodes allow stimulation of a larger part of the heart.

Further, retriggering capability is provided to allow the delivery of a burst of pulses for any desired duration. The delivery being controlled by a user pressing and holding a button or key on the programmer. In a preferred embodiment the pulse train is 2–5 seconds long.

Alternative embodiments of the invention would provide higher rates of delivery of the fibrillation pulses, for instance at 8 to 16 milliseconds. Lower pulse amplitudes would result in less energy delivery, and higher output impedance with provide for better current limiting.

The above description is intended by way of example only and is not intended to limit the present invention in any way except as set forth in the following claims.

We claim:

1. A defibrillator/cardioverter system for use in inducing fibrillation comprising:

external programming means for transmitting a fibrillation command signal;

an implantable pulse generator comprising fibrillation pulse train circuitry means for generating a fibrillation inducing pulse train in response to a received fibrillation command signal, each pulse of said pulse train having a pulse width $t_w$ and nominal voltage $V_n$ and a delay time $t_d$ from the immediately preceding pulse, the pulse generator also having multiphasic switching means for receiving said pulse train and outputting an output pulse train having pulses of predetermined phase; and defibrillation electrodes for delivering the output pulse train to the heart.

2. The system of claim 1, wherein said delay time $t_d$ is set between approximately 30–50 milliseconds, said pulse width $t_w$ is approximately 1.1 milliseconds, and said nominal voltage $V_n$ is approximately between 9 to 15 volts for each of the pulses, said pulse train being approximately 2–5 seconds long.

3. The system of claim 1, wherein said implantable pulse generator includes logic means which in response to said fibrillation command signal causes said fibrillation pulse train circuitry means to generate said fibrillation inducing pulse train with a predetermined pulse width and a predetermined time delay.

4. The system of claim 1, wherein said multiphasic switching means is operable for outputting said output pulse train with monophasic pulses.

5. The system of claim 1, wherein said multiphasic switching means is operable for outputting said output pulse train with multiphasic pulses.

6. A method for generating a fibrillation waveform comprising the steps of:

determining an initial voltage of a first phase of said waveform, an end voltage of the first phase of said waveform, and time duration ratios of subsequent phases with respect to the first phase of said waveform;

charging a capacitor to the initial voltage;

discharging the capacitor to the end voltage over a phase duration to end the first phase;

deriving a subsequent phase duration from the previous phase duration and said time duration ratios; and discharging the capacitor to a subsequent voltage across a pair of terminals for the subsequent phase duration.

7. The method according to claim 6, wherein said initial voltage is applied to the pair of terminals through a polarity reversing switch, further comprising, after the first phase discharging step, reversing said polarity reversing switch t produce an inverted voltage as applied across said pair of terminals.

8. The method according to claim 6, wherein the subsequent voltage is equal in magnitude to the end voltage.

9. A method for generating a time ratiometric fibrillation waveform comprising the steps of:

setting an initial voltage level of a capacitor corresponding to an initial voltage level of a first phase of a fibrillation waveform;

setting for each phase in the waveform subsequent to the first phase a desired time ratio of the duration of the respective phase to a time duration of the first phase of the waveform;

setting an end voltage level of the first phase of a waveform;

charging the capacitor to the initial voltage level;

discharging the capacitor from the initial voltage level to the end voltage level to cause the first phase of the waveform;

determining the time duration of the first phase of the waveform;

computing time durations of subsequent phases of the waveform based on the time duration of the first phase and the ratios of the time durations of the subsequent phases relative to the first phase;

controlling the discharge of the capacitor according to the time durations of subsequent phases to generate the subsequent phases of the fibrillation waveform.

10. A method for generating a fibrillation waveform to the heart of a patient, said method comprising the steps of:

loading into a voltage threshold register, a value corresponding to a desired initial voltage of a first phase of the waveform;

comparing said value corresponding to a desired initial voltage to a voltage currently across a capacitor;

loading a charge command bit code into a command register;

charging the capacitor whenever the charge command bit code is in the command register and the voltage across the capacitor is less than the value corresponding to the desired initial voltage of the first phase;

terminating said charging of the capacitor when the voltage across said capacitor reaches the desired initial of the first phase;

loading into the voltage threshold register, a value corresponding to the desired termination voltage of the first phase;

loading a fire command bit code into the command register;

discharging the capacitor through the patient's heart in response to the fire command bit code being loaded into the command register thereby commencing the first phase of the waveform;

terminating said discharging of the capacitor upon said voltage across the capacitor decaying to the value most recently loaded into the voltage threshold register thereby terminating said first phase;

determining the time duration of the first phase;

storing said time duration in a data buffer;

selecting a pulse width percentage corresponding to a next phase of the waveform;

multiplying the time duration of the first phase by said pulse width percentage to thereby determine the time duration of the next phase of the waveform;

further discharging said capacitor through the patient's heart for the time duration resulting from said step of multiplying;

repeating the steps of selecting, multiplying, and further discharging for subsequent phases of the waveform.

11. The method of claim 10, wherein the step of further discharging further comprises the step of alternating the polarity of each phase such that successive phases have opposite polarity.

12. Apparatus for generating a multiphasic waveform, said apparatus comprising:

capacitive means for storing electrical energy;

programmable processing means for controlling the charging and discharging of said capacitive means;

at least one addressable register for storing command bit codes and waveform parameters provided by said programmable processing means;

timing means for measuring the time duration of the first phase of the multiphasic waveform;

data storage means responsive to said timing means for storing a value corresponding to the time duration of the first phase;

comparison means for comparing voltage-related waveform parameters stored in said at least one addressable register to the voltage across the capacitive means;

multiplexing means connected to said at least one register for selectively choosing a waveform parameter corresponding to a desired pulse width percentage;

multiplication means responsive to the selectively chosen waveform parameter from said multiplexing means and also responsive to said timing means for multiplying the time duration of the first phase by the desired pulse width percentage and for generating a signal indicative of the result thereof;

at least two defibrillation electrodes located near a patient's heart;

switch means for selectively discharging said capacitive means through the heart via said at least two defibrillation electrodes;

pulse control means for controlling said switch means to discharge the capacitive means in accordance with voltage-related waveform parameters corresponding to pulse width percentages for subsequent phases, said pulse control means being responsive to the comparison means, the timing means, the multiplication means, and said at least one register;

charging means for charging the capacitive means and;

charge control means responsive to the comparison means and responsive to said at least one register, for controlling the charging means.

13. The apparatus of claim 12, wherein said capacitive means is a 125 to 150 microfarad capacitor.

14. The apparatus of claim 12 wherein said comparison means comprises a comparator, a voltage divider, and a digital-to-analog converter; said voltage divider providing the comparator with a first input voltage proportional to, but less than, the voltage across the capacitive means, and said digital-to-analog converter provides the comparator with a second input voltage proportional to the value of a voltage-related parameter currently stored in said at least one addressable register.

* * * * *